United States Patent
Bardy

Patent Number: 5,261,400
Date of Patent: Nov. 16, 1993

[54] DEFIBRILLATOR EMPLOYING TRANSVENOUS AND SUBCUTANEOUS ELECTRODES AND METHOD OF USE

[75] Inventor: Gust H. Bardy, Seattle, Wash.

[73] Assignee: Medtronic, Inc., Minneapolis, Minn.

[21] Appl. No.: 834,446

[22] Filed: Feb. 12, 1992

[51] Int. Cl.⁵ ............................................. A61N 1/39
[52] U.S. Cl. ...................................................... 607/5
[58] Field of Search ................... 128/419 D, 784, 785, 128/786

[56] References Cited

U.S. PATENT DOCUMENTS

| | | | |
|---|---|---|---|
| 4,727,877 | 3/1988 | Kallok | 128/419 D |
| 4,922,927 | 5/1990 | Fine et al. | 128/786 |
| 4,953,551 | 9/1990 | Mehra et al. | 128/419 D |
| 5,014,696 | 5/1991 | Mehra | 128/419 D |
| 5,144,960 | 9/1992 | Mehra et al. | 128/785 |

FOREIGN PATENT DOCUMENTS 0453761  3/1991  European Pat. Off. ..... 128/419 PG Primary Examiner—Kyle L. Howell
Assistant Examiner—George Manuel
Attorney, Agent, or Firm—Reed A. Duthler; Harold R. Patton

[57] ABSTRACT

A defibrillation pulse generator and lead system particularly adapted to allow for implant via a single incision. The electrode system consists of a right ventricular electrode and a single subcutaneous electrode, which is preferably located on the housing of the implantable defibrillator. The defibrillator is preferably implanted in the left pectoral region of the heart, and is employed as the cathodal electrode during the initial phase of a bi-phasic defibrillation pulse applied between the two electrodes.

6 Claims, 1 Drawing Sheet

DEFIBRILLATOR EMPLOYING TRANSVENOUS AND SUBCUTANEOUS ELECTRODES AND METHOD OF USE

BACKGROUND OF THE INVENTION

The present invention relates to medical electrical leads generally, and more particularly to implantable defibrillation electrodes and leads.

Early concepts of implantable defibrillators, such as disclosed in Reissue U.S. Pat. No. 27,652 by Mirowski et. al., envisioned an electrode system employing a ventricular endocardial electrode and a plate electrode mounted to the heart or implanted subcutaneously. However, commercially available implantable defibrillators employ epicardial electrodes, the installation of which requires a thoracotomy.

It is generally understood that it would be desirable to produce an implantable defibrillation system which entirely avoids the necessity of a thoracotomy, and there has been substantial work directed towards development of such systems, as disclosed in U.S. Pat. No. 4,727,877 issued to Kallok, U.S. Pat. No. 4,708,145 issued to Tacker et. al., and as disclosed in allowed U.S. application Ser. No. 07/284,955 filed Dec. 15, 1988 by Bardy, for an "Endocardial Defibrillation Electrode System", incorporated herein by reference in its entirety. Electrode systems of this type are presently in clinical evaluation, pending FDA approval.

Other endocardial defibrillation electrodes are disclosed in U.S. Pat. No. 4,481,953 issued to Gold et. al., U.S. Pat. No. 4,161,952 issued to Kinney et. al., U.S. Pat. No. 4,934,049 issued to Kiekhafer et. al. and in U.S. Pat. application Ser. No. 07/479,928, filed Feb. 14, 1990 by Holleman et. al., for an "Implantable Electrode and Method for Fabrication", all of which are incorporated herein by reference in their entireties. The Kinney, Gold and Kiekhafer patents and the Holleman et. al. application all disclose endocardial defibrillation leads employing defibrillation electrodes fabricated from elongated coils of biocompatible metal, mounted exposed to the exterior of the defibrillation lead, for location in the right ventricle and other locations within the heart. U.S. Pat. No. 4,641,656. issued to Smits and the above cited Bardy application both disclose a variety of endocardial defibrillation electrodes intended for use in the atrium, ventricle and coronary sinus, all of which employ electrodes taking the form of elongated coils of conductive biocompatible metals.

The endocardial leads set forth in the above cited references are generally employed with one or more additional endocardial or subcutaneous electrodes. In general, there has been a trend toward lead systems employing three or more such electrodes in order to reduce defibrillation thresholds to an acceptable level. In the Tacker and Kallok references, lead systems which employ three or more electrodes, sequentially paired with one another are discussed. In the Bardy application and the Smits patent, lead systems in which three or more electrodes are used simultaneously to deliver a defibrillation pulse are disclosed.

The subcutaneous leads employed in the systems as discussed above may be fabricated using metal mesh electrodes, as disclosed in U.S. Pat. No. 4,765,341, issued to Mower et. al., coiled metal wire electrodes as disclosed in U.S. Pat. No. 4,817,634, issued to Holleman et. al. or may be the metal enclosure of the defibrillator as disclosed in the above-cited Kallok patent.

A variety of pulse wave forms and polarities have been suggested. Monophasic capacitive discharge pulses are disclosed in the above cited Mirowski reissue patent. Biphasic pulses are disclosed in U.S. Pat. No. 4,953,551, issued to Mehra et. al. Damped sinusoidal pulses are disclosed in U.S. Pat. No. 4,834,100, issued to Charms.

A return to lead systems employing only two electrodes is suggested in U.S. Pat. No. 4,922,927, issued to Fine et. al. This patent proposes the use of an electrode system as in the above-cited Mirowski reissue Patent, using a right ventricular electrode and a subcutaneous electrode, which may correspond to prior art subcutaneous electrodes or may be the metal enclosure of the defibrillator. The right ventricular electrode carries an elongated coil electrode fabricated of a copper-zirconium alloy coated with iridium oxide. The use of biphasic pulses in such a two electrode system is also recommended. However, no recommendation is given as to the preferred polarity for the leading phase of the biphasic pulse. The Fine patent states that defibrillation thresholds as low as 7-10 joules may be achieved with such an endocardial lead in conjunction with a subcutaneous electrode, apparently implanted in proximity to the ventricles rather than pectorally.

SUMMARY OF THE INVENTION

The present invention is directed toward the provision of a defibrillator employing endocardial and subcutaneous electrodes and which delivers an asymmetrical biphasic capacitive discharge pulse between the two electrodes. In the preferred embodiment of the invention, the endocardial electrode is located in the right ventricle and the subcutaneous electrode is located in the left, pectoral region of the chest, rather than at the level of the ventricles. The subcutaneous electrode is preferably the portion of the metal enclosure of the defibrillator which faces inwardly, and the initial phase of the pulse is delivered using the subcutaneous electrode as the cathode (coupled to the negatively charged terminal of the output capacitor during the initial phase). The biphasic pulse is preferably of the type illustrated in U.S. Pat. No. 4,953,3,551, issued to Mehra et. al. on Sep. 4, 1990. A defibrillator, operated in accordance with the present invention has been found to result in a substantially lowered defibrillation pulse threshold as compared to other similar systems. Furthermore, the present invention provides its advantages even when conventional defibrillation electrode materials are employed for the endocardial lead, e.g. platinum, and thus allows the use of the invention in conjunction with previously implanted ventricular defibrillation electrode leads.

DETAILED DESCRIPTION OF THE PREFERRED EMBODIMENT

Figure 1:
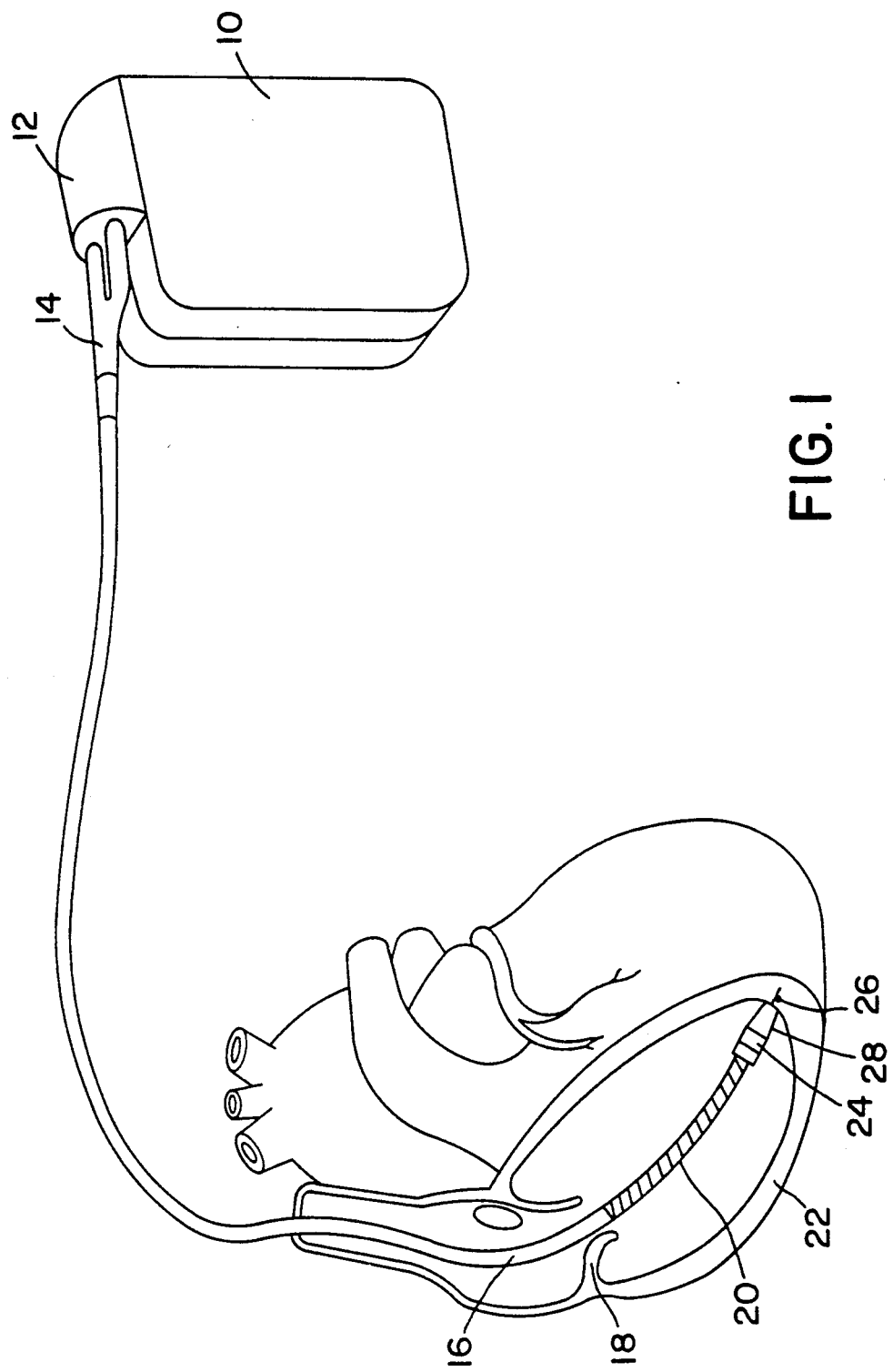
FIG. 1 illustrates the implantable defibrillator and lead according to the present invention.

FIG. 1 illustrates the defibrillator and lead according to the present invention. The lead takes the form of the lead disclosed in the above cited allowed application by Bardy, and includes an elongated insulative lead body 16, carrying three concentric coiled conductors, separated from one another by tubular insulative sheaths.

Located on adjacent the distal end of the lead are a ring electrode 24, an extendable helix electrode 26, mounted retractably within an insulative electrode head 28, and an elongated coil electrode 20. Each of the electrodes is coupled to one of the coiled conductors within the lead body 16. Electrodes 24 and 26 are employed for cardiac pacing and for sensing ventricular depolarizations. At the proximal end of the lead is a bifurcated connector which carries three electrical connectors, each coupled to one of the coiled conductors. The defibrillation electrode 20 may be fabricated from platinum, platinum alloy or other materials known to be usable in implantable defibrillation electrodes.

An implantable defibrillator 10 is shown in combination with the lead, with the lead connector assembly 14 inserted into the connector block 12 of the defibrillator 10. A specific example of a defibrillation pulse generator which may be used in conjunction with the present lead to deliver biphasic pulses is disclosed in U.S. Pat. No. 4,953,551, issued to Mehra et. al. on Sep. 4, 1990, incorporated herein by reference in its entirety. In order to deliver this pulse according to the present invention, it is necessary to connect electrode 20 such that it serves as the anode during the initial phase of the defibrillation pulse. The portion of the housing of the defibrillator which faces inward must be connected to serve as the cathode during delivery of the first phase of the pulse. Insulation of the outward facing portion of the defibrillator housing may be accomplished using a plastic coating, for example parylene or silicone rubber, as is currently employed in some unipolar cardiac pacemakers.

The electrode system and method of the present invention has the important advantages of simplicity of construction and of use. Unlike systems involving subcutaneous electrodes located at approximately the level of the heart, the pectoral location of the electrode of the present invention allows for implant using only a single incision. This benefit is accomplished without the necessity of fabrication of defibrillation leads carrying multiple defibrillation electrodes and without the necessity of employing exotic new electrode materials while still retaining the low defibrillation thresholds attributed to the prior art exotic metal and multiple electrode leads.

This particular electrode configuration also has advantages in regard to optimizing current distribution with respect to the heart. The right ventricular lead, as a practical matter generally lies along the posterior, inner wall of the right ventricle. The pectoral location of the defibrillator is located anterior to the heart. The bulk of the mass of the ventricles lies between the electrodes. Thus, in this two electrode system, the pectoral site is close to ideal. In a system, employing, for example, both right ventricular and superior vena cava electrodes in conjunction with the defibrillator housing as suggested in European Patent Application No. 0453761, the pectoral site is believed to be less optimal. In such a system it is believed that the current pathway between the superior vena cava electrode and the pectoral electrode would tend to divert energy away from the ventricles.

In acute human clinical testing, the inventor has determined that a defibrillator/lead system according to the present invention provides effective defibrillation at pulse energies of approximately eight joules. These results were obtained using a Medtronic right ventricular defibrillation lead, carrying a single platinum coil defibrillation electrode and the inward facing half of a titanium housing of an Medtronic Model 7217 implantable defibrillator. The half-housing has a total exposed surface area of approximately 100 square centimeters, the planar, major surface having an area of approximately 70 square centimeters. The half-housing was located in the left infraclaricular pectoral region and was employed as the cathodal electrode during the initial phase of the biphasic defibrillation pulse.

There are major efforts presently underway to reduce the size of current implantable defibrillators to further simplify implant and enhance patient comfort. As the devices become smaller, it is anticipated that the surface areas of the defibrillator housings may become small enough to interfere ability of the housing to function efficiently as the subcutaneous defibrillation electrode. In such cases, it is envisioned that the surface area of the subcutaneous electrode may be increased by means of a supplemental plate electrode electrically coupled to the defibrillator housing or employed as an electrode in place of the defibrillator housing. This supplemental electrode may be simply placed in the pectoral implant site adjacent the defibrillator or may in some cases be clipped or otherwise attached to the inward facing surface of the defibrillator housing.

In conjunction with the above specification, I claim:

1. An apparatus for defibrillating a human heart, comprising:
   a first defibrillation electrode means for location in the right ventricle of said human heart;
   an implantable defibrillation pulse generator having a housing and having a first output coupled to said first defibrillation electrode; and
   a second defibrillation electrode comprising a conductive portion of said housing of said defibrillation pulse generator and coupled to a second output of said defibrillation pulse generator; and
   wherein said defibrillation pulse generator is coupled only to said first and second defibrillation electrodes and comprises means for delivering a biphasic defibrillation pulse having first and second phases, to said first and second electrodes, such that during said first phase of said biphasic pulse, said first electrode is the anode and said second electrode is the cathode.

2. An apparatus for defibrillating a human heart, comprising:
   a first defibrillation electrode means for location in the right ventricle of said human heart;
   a second defibrillation electrode means for subcutaneous location;
   an implantable defibrillation pulse generator coupled to said first and second defibrillation electrodes; and
   wherein said defibrillation pulse generator comprises means for delivering a biphasic defibrillation pulse having first and second phases, only to said first and second electrodes, such that during said first phase of said biphasic pulse, said first electrode is the anode and said second electrode is the cathode.

3. An apparatus according to claim 1 or claim 2 wherein said first defibrillation electrode comprises a defibrillation electrode fabricated of platinum or platinum alloy.

4. A method of defibrillating a patient's heart, comprising:
   implanting a transvenous electrode lead in the right ventricle of said patient's heart;
   subcutaneously implanting a defibrillation pulse generator, having a housing and employing a portion of said metallic housing as a defibrillation electrode, in the left pectoral region of said patient's body such that said portion of said housing is facing inward; and delivering a biphasic defibrillation pulse only between said transvenous electrode and said portion of said housing of said defibrillation pulse generator such that during the first phase of said pulse, said transvenous electrode is the anode and said portion of said defibrillation pulse generator's housing is the cathode.

5. A method of defibrillating a patient's heart, comprising:

implanting transvenous electrode lead in the right ventricle of said patient's heart;

subcutaneously implanting a subcutaneous defibrillation electrode, in the left pectoral region of said patient's body; and delivering a biphasic defibrillation pulse only between said transvenous electrode and said subcutaneous defibrillation electrode such that during the first phase of said pulse, said transvenous electrode is the anode and said subcutaneous defibrillation electrode is the cathode.

6. A method according to claim 4 or claim 5 wherein said step of implanting said first transvenous electrode lead comprises implanting a lead having a defibrillation electrode fabricated of platinum or platinum alloy.

* * * * *